(12) United States Patent
Beug-Deeb et al.

(10) Patent No.: US 11,058,112 B2
(45) Date of Patent: Jul. 13, 2021

(54) METHODS AND COMPOSITIONS FOR CLEANING AND DISINFECTING SURFACES

(71) Applicant: MARIA BEUG-DEEB INC., Roswell, GA (US)

(72) Inventors: Maria U. D. Beug-Deeb, Roswell, GA (US); Thomas M. Deeb, Roswell, GA (US)

(73) Assignee: Maria Beug-Deeb, Inc., Roswell, GA (US)

( * ) Notice: Subject to any disclaimer, the term of this patent is extended or adjusted under 35 U.S.C. 154(b) by 38 days.

(21) Appl. No.: 16/543,523

(22) Filed: Aug. 17, 2019

(65) Prior Publication Data

US 2019/0364893 A1    Dec. 5, 2019

Related U.S. Application Data

(60) Continuation of application No. 14/735,553, filed on Jun. 10, 2015, now Pat. No. 10,426,164, which is a division of application No. 14/210,780, filed on Mar. 14, 2014, now abandoned.

(60) Provisional application No. 61/792,061, filed on Mar. 15, 2013.

(51) Int. Cl.
| | |
|---|---|
| *A01N 37/36* | (2006.01) |
| *A61L 2/18* | (2006.01) |
| *A61L 2/22* | (2006.01) |
| *A61L 2/23* | (2006.01) |
| *C11D 3/20* | (2006.01) |
| *C11D 3/48* | (2006.01) |
| *C11D 9/00* | (2006.01) |
| *C11D 9/26* | (2006.01) |

(52) U.S. Cl.
CPC ............... *A01N 37/36* (2013.01); *A61L 2/18* (2013.01); *A61L 2/22* (2013.01); *A61L 2/23* (2013.01); *C11D 3/2086* (2013.01); *C11D 3/48* (2013.01); *C11D 9/007* (2013.01); *C11D 9/26* (2013.01); *A61L 2202/24* (2013.01)

(58) Field of Classification Search
CPC ........... A01N 37/36; C11D 3/48; C11D 9/007
See application file for complete search history.

(56) References Cited

U.S. PATENT DOCUMENTS

| | | | | | |
|---|---|---|---|---|---|
| 4,747,977 | A | * | 5/1988 | Whitehead | C11D 3/43 510/321 |
| 4,919,838 | A | * | 4/1990 | Tibbetts | C11D 10/04 510/120 |
| 5,709,546 | A | * | 1/1998 | Waggoner | A61C 1/0076 433/82 |
| 6,500,861 | B1 | * | 12/2002 | Wider | A61K 47/12 514/546 |

OTHER PUBLICATIONS

Nutribiotic (https://web.archive.org/web/20121020015448/http://www.nutribiotic.com/coconut-soap-peppermintandbergamot-32oz.html) available online Oct. 20, 2012, pp. 1-4. (Year: 2012).*
Examination Report: Canadian Application No. 2,942,000; dated Aug. 14, 2020.
Examination Report No. 1: Australian Application No. 2018229488; dated May 31, 2019.
Examination Report No. 2: Australian Application No. 2028229488; dated Aug. 1, 2019.
Notice of acceptance for patent application: Australian Application No. 2028229488; dated Jan. 15, 2020.
Saffari, V. R et al., "Effects of EDTA, citric acid, and tartaric acid application on growth, phytoremediation potential, and antioxidant response of *Calendula officinalis* L. in a cadmium-spiked calcareous soil", International Journal of Phytoremediation, DOI: 10.1080/15226514.2020.1754758, Abstract, p. 1, line 3.

* cited by examiner

*Primary Examiner* — Andrew S Rosenthal
(74) *Attorney, Agent, or Firm* — David W. Ladner; Ladner Patent Management LLC

(57) ABSTRACT

This application relates to compositions for cleaning and disinfecting unclean surfaces that are contaminated, typically with bacteria, viruses, yeast and molds. Broadly speaking contaminated surfaces includes hard and soft surfaces such as those found in household environments, in industrial environments, and hospitals, as well as surfaces of food products such as fruits, vegetables and meat. Further, the compositions can be prepared with naturally occurring components that are classified as generally considered as safe (GRAS) by the US FDA and/or comply with National Organic Production (NOP) standards of the USDA and can therefore be used in situations where such a classification is required such as organic food production.

7 Claims, 3 Drawing Sheets

METHODS AND COMPOSITIONS FOR CLEANING AND DISINFECTING SURFACES

CROSS REFERENCE TO RELATED APPLICATION

This Application is a continuation of co-pending application Ser. No. 14/735,553 filed Jun. 10, 2015 which claims the benefit of application Ser. No. 14/210,780, filed Mar. 14, 2014, now abandoned, which claims priority to U.S. Provisional Application No. 61/792,061 filed on Mar. 15, 2013; all of which are incorporated herein by reference in their entirety.

FIELD OF THE INVENTION

This application relates to the problem of cleaning and disinfecting unclean surfaces that are contaminated, typically with bacteria, viruses, yeast and molds.

BACKGROUND

Broadly speaking contaminated surfaces includes hard surfaces and soft surfaces such as those found in household environments, in industrial environments, surfaces of food products such as fruits, vegetables and meat, and exterior and interior surfaces of the human body that may become exposed to microbes. It also pertains to exterior and interior and exterior surfaces of equipment that can be contaminated, such as those found in the food industry or the medical equipment found in hospitals and health care facilities, as well as surfaces of implanted devices such as catheters, prosthetic cardiac valves and intrauterine devices.

All such surfaces are at risk of contamination if they are exposed to non-sterile water, air. or soil or other environments where microbes are present.

There is a growing scientific recognition that bacterial organisms which actively populate these common surfaces may form organized communities called biofilms. Bacterial cells forming these biofilm communities assume a biological phenotype that is markedly different than their corresponding planktonic (non-surface attached, or free-swimming) bacterial analogs (W. G. Characklis, "Microbial Biofouling Control" in Biofilms, Characklis and Marshall, eds., Wiley & Sons, 1990, J. W. Costerton, Ann. Rev. Microb. 49:7110-7145, 1995). Biofilms are a special form of contamination that have been shown to require as much 1000 time the dose of routine biocides in order to eradicate the microorganism contained within, as compared to planktonic forms.

The significantly decreased susceptibility of biofilm cells to biocides has been documented in numerous studies. See for example: A B. Ronner, et al., J. Food Prot. 56:750-758, 1993; J. W. Costerton, supra, 1995, P. Gilbert and M. R. W. Brown, Microbial Biofilms, Lappin-Scott and Costerton, Eds., University Press, 1995; S. Oie, et al., Microbios. 85:223-230, 1996; J. R. Das, et al., Changes In Biocide Susceptibility of Bacteria Following Attachment to Surfaces, poster presentation, American Society of Microbiology Conference on Microbial Biofilms, Snowbird, Utah, 1997; C. Ntasama-Essomba, et al., Veter. Res. 28:353-363, 1997, J. W. Costerton, Internat. J. Antimicrob. Agents 11:217-221, 1999.

Because of the nature of biofilms, today it is common practice that in order to treat and remove or reduce contamination, a 4-step cleaning process is required. This process involves cleaning the surface with a surfactant containing solution, typically at elevated temperatures with scrubbing action, rinsing of the surface with clean water to remove the cleaning agents and biofilms, followed by treatment of the surface with and antimicrobial for the required time frame, followed by rinsing the surface with clean water to remove the antimicrobial agent and bacteria. This 4-step process is expensive because it requires, labor, energy, water and time which increases the cost of doing business. Further it is known that this 4-step process does not prevent regrowth of the organism as the anti-microbial agent is removed through the process thereby leaving the surface available for re-inoculation, biofilm formation and therefore the ability of microbes to grow and flourish.

Whether the contamination occurs from biofilms or free swimming organisms, there is a need for convenient and less labor intensive methods for decontamination of environmental surfaces.

Most chemical products suitable for use on foodstuff or hard food contact surfaces do not have significant antimicrobial and microbicidal properties. Sanitizing products which exhibit significant antimicrobial and/or microbicidal properties have historically been considered unsafe or suspect as containing ingredients which are not classified by the United States Food and Drug Administration (USFDA) as GRAS (Generally Regarded As Safe) for food contact or as a food additive.

Methods and compositions that are safe for use in the food and healthcare industry, would be particularly useful, especially compositions that would be acceptable in organic food production and processing, which require components that are Generally Recognized as Safe (GRAS) by the United States Food and Drug Administration and/or meet the United States Department of Agriculture's National Organic Program requirements.

SUMMARY

In accordance with the purpose(s) of the invention, as embodied and broadly described herein, the invention relates to a method of cleaning and/or disinfecting a surface comprising contacting the surface with a composition comprising an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and an organic acid selected from the group consisting of citric acid, tartaric acid, lactic acid and malic acid.

In another aspect, the invention relates to a method of removing a biofilm from a surface comprising contacting said surface with a composition comprising an organic surfactant comprising a blend of C4-C24 saturated and unsaturated fatty acid salts, such that the blend comprises at least about 1-6% C6 C10 fatty acids salts, and at least about 30% C12-C14 fatty acid salts; and an organic acid selected from the group consisting of citric acid, tartaric acid, lactic acid and malic acid.

In another aspect, the invention relates to an antimicrobial composition consisting essentially of an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and an organic acid selected from the group consisting of citric acid, tartaric acid, lactic acid and malic acid.

Also disclosed are methods and compositions in which the components of the composition are generally regarded as safe (GRAS) by the US FDA for use on food and/or are acceptable under the regulations of the USDA National Organic Production (NOP).

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
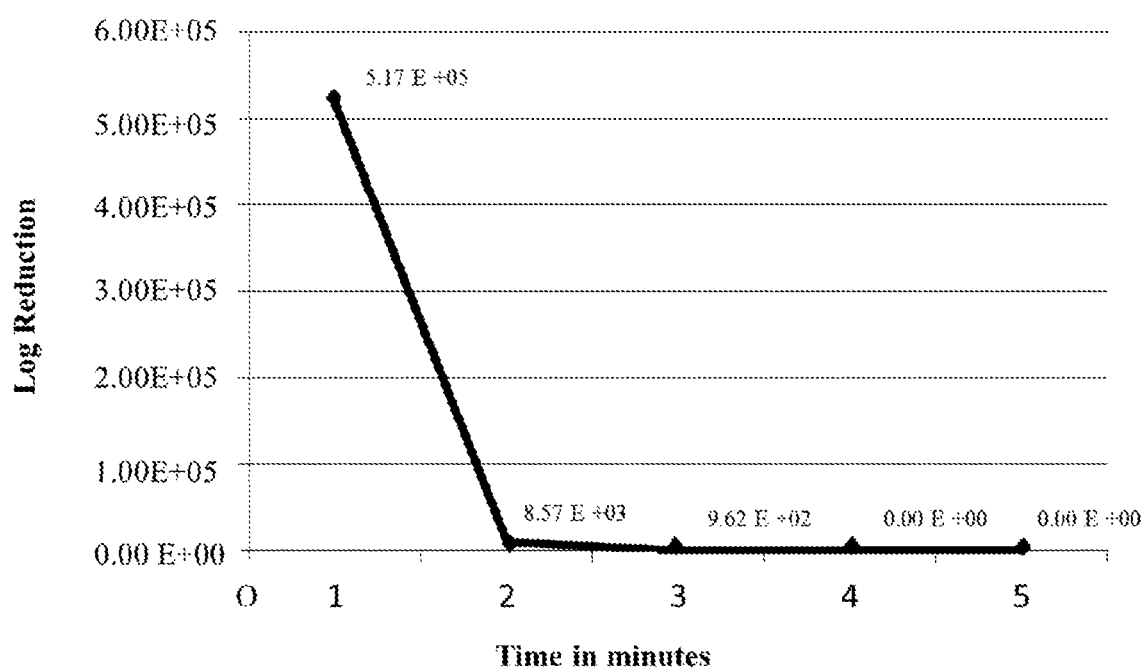
FIG. 1 shows the log reduction vs. time of an *E. coli* contaminated surface that has been treated with a composition comprising citric acid and saponified coconut oil.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt %) of a component, unless specifically stated to the contrary, is based on the total weight of the formulation or composition in which the component is included.

As used herein, the term "biofilm" or "biofilm EPS" refers to an aggregate of microorganisms in which cells adhere to each other on a surface. These adherent cells are frequently embedded within a self-produced matrix of extracellular polymeric substance (EPS), a generally sticky rigid structure of polysaccharides, DNA, and other organic contaminants A biofilm layer is anchored firmly to a surface and provides a protective environment in which microorganisms grow. Bacteria, viruses, yeasts, molds, and fungi contained in the biofilms can become dormant and therefore reduce their uptake of nutrients and/or antimicrobial agents. Biofilms have been found to be involved in a wide variety of microbial infections in the body, such as urinary tract infections, catheter infections, middle-ear infections, formation of dental plaque, gingivitis, coating contact lenses, and serious and potentially lethal processes such as endocarditis, infections in cystic fibrosis, and infections of permanent indwelling devices such as joint prostheses and heart valves. Bacterial biofilms may impair cutaneous wound healing and reduce topical antibacterial efficiency in healing or treating infected skin wounds. Biofilms are also present on the removed tissue of 80% of patients undergoing surgery for chronic sinusitis. Biofilms can also be formed on the inert surfaces of implanted devices such as catheters, prosthetic cardiac valves and intrauterine devices.

Additional discussions of biofilms are found in the following which are incorporated herein by reference:

Hall-Stoodley L, Costerton J W, Stoodley P (February 2004). "Bacterial biofilms: from the natural environment to infectious diseases". Nature Reviews. Microbiology 2 (2): 95-108.

Lear, G; Lewis, G D (editor) (2012). Microbial Biofilms: Current Research and Applications. Caister Academic Press. ISBN 978-1-904455-96-7.

Stewart P S, Costerton J W (July 2001). "Antibiotic resistance of bacteria in biofilms". Lancet 358 (9276): 135-8.

Parsek M R, Singh P K (2003). "Bacterial biofilms: an emerging link to disease pathogenesis". Annual Review of Microbiology 57: 677-701.

Sanclement J, Webster P, Thomas J, Ramadan H (2005). "Bacterial biofilms in surgical specimens of patients with chronic rhinosinusitis". Laryngoscope 115 (4): 578-82.

Ramadan H H, Sanclement J A, Thomas J G (March 2005). "Chronic rhinosinusitis and biofilms". Otolaryngology—Head and Neck Surgery 132 (3): 414-7.

Bendouah Z, Barbeau J, Hamad W A, Desrosiers M (June 2006). "Biofilm formation by *Staphylococcus aureus* and *Pseudomonas aeruginosa* is associated with an unfavorable evolution after surgery for chronic sinusitis and nasal polyposis". Otolaryngology—Head and Neck Surgery 134 (6): 991-6.

Lynch A S, Robertson G T (2008). "Bacterial and fungal biofilm infections". Annual Review of Medicine 59: 415-28.

Allison, D. G. (2000). Community structure and co-operation in biofilms. Cambridge, UK: Cambridge University Press. ISBN 0-521-79302-5.

Lynch, James F.; Lappin-Scott, Hilary M.; Costerton, J. W. (2003). Microbial biofilms. Cambridge, UK: Cambridge University Press. ISBN 0-521-54212-X.

Fratamico, M. (2009). Biofilms in the food and beverage industries. Woodhead Publishing Limited. ISBN 978-1-84569-477-7.

As used herein, the term "antimicrobial" refers to an agent or a property of an agent that kills microorganisms or inhibits their growth. The microorganisms may be bacteria, fungi, viruses, or parasites such as protozoa. The antimicrobial agent can be referred to as a biocide, bactericide, slimicide, algicide, fungistat, mildewstat, and the like, depending on the organism that is killed or inhibited by the agent.

As used herein, the term "slime" refers to a layer of biofilm or biofilm EPS.

As used herein, the term "natural oil" refers to any of the edible vegetable oils derived from natural sources and includes coconut oil, palm oil, soybean oil, corn oil canola (rapeseed) oil, peanut oil, safflower oil, cotton seed sunflower oil and the like. The natural oils may be optionally hydrogenated.

As used herein, the term "environmental surface" includes washable hard, nonporous surfaces found in hospitals, medical and dental offices, nursing homes, health care facilities, ultrasonic baths (ultrasonic cleaning units), federally inspected food processing facilities, federally inspected meat and poultry plants, wineries, breweries, beverage manufacturing facilities, dairy farms, swine farms, poultry and turkey farms, farm premises, hatcheries, refrigerated trucks, kennels, pet animal quarters, zoos, pet shops, animal laboratories, veterinary facilities, animal care facilities, transportation terminals, hotels and motels, factories, business and office buildings, barber shops, salons, boats, ships, campers, trailers, mobile homes, homes, kitchens, bathrooms, household areas, cars, buses, trains, taxis, airplanes, restaurants, bars, cafeterias, institutional kitchens, food preparation and storage areas, convenience stores, food storage areas, tattoo parlors, public rest rooms, institutions, schools and colleges, athletic facilities, sports facilities, gym rooms, locker rooms, dressing rooms, shower and bath areas, exercise equipment, large, inflatable, non-porous plastic and rubber structures (animals, promotional items, moonwalk, slides, obstacle course play equipment, exercise equipment and wrestling mats.

Examples of such surfaces include medical machines (X-ray, MRIs, CAT scanners and the like), noncritical medical devices and equipment surfaces; steam sterilizer water reservoirs, steam sterilizer water reservoir tubing; water reservoir tanks, water reservoir pipes, tanks, and piping systems used in food processing; floors, walls, countertops, stovetops, sinks, appliances, refrigerators (exteriors), plastic and other nonporous cutting boards and chopping blocks; coolers, ice chests; nonresidential refrigerator bins (exteriors) for meat, fruit, vegetable and egg; food processing equipment (k-pac equipment, injectors, slicers, knives, steel mesh gloves, deboners, saws, grinders, cutters, racks, dairy equipment, interlocking belts, outside surfaces of kitchen equipment, beer fermentation and holding tanks, brewery pasteurizers, wine fermentation tanks, beverage dispensing equipment, beverage transfer lines, bottling or premix dispensing equipment); drinking water coolers, ice making machines, transfer line tubing, water lines, watering systems, farm animal nipple drinkers; cabinets, highchairs, garbage cans, garbage storage areas, refrigerated storage and display equipment (exteriors), tables, picnic tables (non-wooden and finished/sealed or painted), outdoor furniture, chairs, desks, telephones, doorknobs, shower stalls, tubs and glazed tiles, whirlpool bathtubs, bathtubs, sinks, urinals, exterior toilet bowl surfaces, other bathroom fixtures; kennel runs, cages, waterers and feeders, automatic feeders, hauling equipment, dressing plants, loading equipment, farrowing barns and related areas (nursery blocks, creep areas), chutes, feed racks, mangers, troughs, fountains and waterers, forks, shovels, scrapers, barns, pens, stalls, facilities and fixtures occupied or traversed by animals, hatchery areas (egg receiving and holding, setter room, tray dumping, chick holding, processing and loading), trays, buggies, racks, egg flats, poultry buildings, ceilings, sidewalls and floors, drinkers and other poultry house related equipment; coils and drain pans of air conditioning and refrigeration equipment and heat pumps, conductive flooring; nonporous salon/barber tools and instruments (combs, brushes, scissors, blades, pedicure and manicure instruments, pedicure and manicure tubs); and other hard nonporous surfaces that are made of metal, stainless steel, glazed porcelain, glazed ceramic, sealed stone, hard fiberglass (bathtubs, tubs, shower stalls, and sinks), plastic (such as polystyrene, polypropylene), glazed porcelain tiling, enameled surfaces, finished/sealed and painted woodwork, finished floors, Formica®, vinyl and plastic upholstery and the like.

As used herein, the term "Clean-in-Place Technology" or "CIP" refers to industrial methods and equipment for cleaning the interior surfaces of processing vessels, pipes, and associated hardware, without the necessity of disassembling the equipment. CIP is frequently used in processing plants to clean pipes, storage tanks, workspaces and conveyance systems between production cycles of different food stuffs and products. Industries and equipment that utilize Clean-in-Place (CIP) technology include those that require frequent and high quality of cleaning and sanitation, such as: brewing, dairy, pharmaceutical, beverage, processed foods, and cosmetics. CIP systems are designed to fit the specific needs of the equipment and may utilize high pressure turbulent gas flow, high flow-rate solvent, reverse flow valves, high pressure or energy spray, high or elevated temperature, application of chemical detergents and filtration sampling systems and sensors.

As used herein, the term "organic acid" is refers to any carboxylic acid, including those which are derived from sources in nature, such as acetic, citric acid, tartaric acid, malic acid, lactic acid and the like.

As used herein, the term "NOP" refers to the USDA National Organic Program which sets regulations and guidance on certification, production, handling, and labeling of USDA organic products.

As used herein, the term "GRAS" pertains to a substance that is classified by regulatory agencies as "generally recognized as safe" under the conditions of its intended use.

As used herein, the term "organic surfactant" refers to a surfactant or a blend of surfactants derived from saponification of a natural oil and includes saponified coconut oil, saponified palm oil, and the like. These surfactants are typically salts of fatty carboxylic acids (carboxylates) with a chain length of from four to twenty-two carbons. The can fully saturated or partially unsaturated. The organic surfactants can be individual salts of a single fatty acid, or a blend of several fatty acid salts.

As used herein, the term "food and beverage industry" refers to industrial and agricultural activities in which food and beverages are prepared, processed and stored, and includes meat and poultry plants, wineries, breweries, beverage manufacturing facilities, dairy farms, swine farms, poultry and turkey farms, farm premises, hatcheries, refrigerated trucks, restaurants, bars, cafeterias, institutional kitchens, convenience stores food preparation areas, food storage areas and food service areas.

As used herein, the term "disinfecting agent" or "disinfectant" refers to a substance with the ability to kill or destroy microorganisms from a surface by direct contact.

As used herein, the term "medical machines" refers to X-ray machines, MRIs, CAT scanners, dental unit water lines, catheters, prosthetic cardiac valves and intrauterine devices and the like, as well as noncritical medical devices and equipment surfaces.

As used herein, the term "organic agriculture", "organic production", "organic farming", or "organically grown" refers to methods of food production which do not involve the use of synthetic pesticides, fertilizers, and in which producers can be certified for adhering to standards and requirements stipulated by the appropriate regulating body, such as the USDA National Organic Program (NOP. For example, in the United States, organic producers comply with the "National List of Allowed and prohibited Substances" which identifies substances which may be used and the non-synthetic substances that cannot be used in organic production.

As used herein, the term "protein surface" refers to meat surfaces, including animal carcasses such beef, swine and poultry carcasses; and the skin surface and surface of butchered cuts of meat. It also refers to exterior and interior surfaces of the human body that may become exposed to microorganisms, such as skin surfaces, especially in and around wounds, the thoracic cavity, the abdominal cavity, synovial spaces, urinary bladder, lungs, sinus cavities, external auditory canal, oral pharynx, pericardial space, and the like.

As used herein, the terms "optional" or "optionally" means that the subsequently described event or circumstance can or cannot occur, and that the description includes instances where said event or circumstance occurs and instances where it does not.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory or a compound prefixed with (+) or d meaning that the compound is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Compositions.

1. Example Compositions

An antimicrobial composition of the invention is a blend of an organic acid such as, but not limited to, citric acid, tartaric acid, lactic acid and malic acid, and a surfactant mixture comprising salts of fatty acids.

The mixture of fatty acids salts can be the direct saponification products of a natural oil such as coconut oil or palm oil, such that the mixture of salts comprises at least from about 1 to about 6% of $C_6$-$C_{10}$ fatty acids salts, (salts of caproic, caprylic, and capric acid), and at least about 30% of $C_{12}$-$C_{14}$ acid salts (salts of lauric and myristic acid). An example of such a mixture is that obtained from saponified coconut oil which comprises salts of the following saturated fatty acids: butyric acid, caproic acid, caprylic acid, capric acid, lauric acid, myristic acid, palmitic acid, steric acid, eicosanoic acid, docosanoic acid and tetracosanoic acid; salts of the following mono-unsaturated fatty acids: palmitoleic acid, oleic acid, eicosenoic acid, erucic acid, and tetrecoseinaoic acid; and the following polyunsaturated fatty acids: linoleic acid, linolenic acid, eleosteric acid, arachidonic acid, eicosapentaenoic acid, docosatetraenoic acid, docosapentaenoic acid, and docosahexaenoic acid.

Alternatively, the surfactant mixture can be fatty acid salts that is a blend of the individual $C_4$-$C_{24}$ saturated and unsaturated fatty acid salts, provided that the blend comprises at least from about 1 to about 6% of $C_6$-$C_{10}$ fatty acids salts, (salts of caproic, caprylic, and capric acid), and at least about 30% of $C_{12}$-$C_{14}$ acid salts (salts of lauric and myristic acid).

The compositions can be prepared from individual aqueous solutions of the organic acid and surfactants, in a ratio of organic acid to surfactant of from about 2:1 to about 10:1 and diluted so that the composition of the aqueous antimicrobial composition comprises from about 40% to about 99% water.

An embodiment of this aspect is an aqueous antimicrobial composition comprising about 10% citric acid, about 2% saponified coconut oil and about 88% water.

Alternatively, the organic acid and surfactants may be dry blended in a ratio of organic acid to surfactant of from about 2:1 to about 10:1 to form a solid antimicrobial composition, and then added to water so that the aqueous antimicrobial composition of the solution comprises from 40% to about 99% water.

An embodiment of this aspect is an solid antimicrobial composition comprising 83% citric acid solid and 17% saponified coconut oil, as the sodium or potassium salt or blends thereof.

The water used for the compositions or forming the aqueous solutions of the compositions is selected based on the end use of the composition. The water source can be normal potable tap water, distilled water, or deionized, sterile (microbe-free) water.

The compositions in this ratio deliver the desired enhanced antimicrobial activity on cleaned surfaces as well as on uncleaned surfaces in the presence of soils, biological materials, and biofilms.

Saponification of natural oils is a well-known procedure known in the art, representing a basic hydrolysis reaction of the triglycerides to produce fatty acid salts and glycerol The base used for the hydrolysis can be sodium hydroxide, potassium hydroxide, lithium hydroxide, calcium hydroxide, magnesium hydroxide, zinc hydroxide and the like, the selection of which determines which cation is associated with the fatty acid carboxylate. Interchange of cations can also be accomplished by single displacement reactions and by ion exchange columns.

It is to be understood that the compositions of the invention can have any of the possible cations associated with the fatty acid salts and that the choice will depend on the aqueous solubility and the desired concentration of the organic acid and surfactant in water.

The compositions of the invention may also include one or more further optional constituents such as known art additives. By way of non-limiting example, such constituents include: water soluble and or dispersible inerts such as silica dioxide or titanium dioxide, further surfactants, particularly surfactants which are useful for the removal of greasy soils, foaming agents and foam stabilizers, coloring agents, including dyes and pigment compositions, fragrances (whether natural or synthetically produced), fragrance adjuvants and/or fragrance solubilizers, viscosity modifying agents including thickeners or gelling agents, pH adjusting agents, pH buffers, antioxidants, water softening agents, further solubilizing agents which might be useful in the solubilization of one or more of the constituents in water, preservative compositions, as well as other known art additives not particularly elucidated here. Such constituents as described above include known art compositions, including those described in McCutcheon's Detergents and Emulsifiers, North American Edition, 1991; Kirk-Othmer, Encyclopedia of Chemical Technology, 3rd Ed., Vol. 22, pp. 346-387, the contents of which are herein incorporated by reference.

The compositions are useful for cleaning and disinfecting unclean surfaces that are contaminated, typically with bacteria, viruses, yeast and molds and like. Broadly speaking contaminated surfaces include hard surfaces such as those found in household environments, in industrial environments, surfaces of food products such as fruits, vegetables and meat, and exterior and interior surfaces of the human body that may become exposed to microbes. The compositions are also useful for cleaning and disinfecting contaminated soft surfaces such as textiles comprised of natural fibers, synthetic fibers, or blends thereof. In addition, the compositions are useful for cleaning interior and exterior surfaces of equipment that are can become contaminated, such as those found in the food industry or on the medical equipment found in hospitals and health care facilities, as well as surfaces of implanted devices such as catheters, prosthetic cardiac valves and intrauterine devices.

All such surfaces are at risk of contamination if they are exposed to non-sterile water, air or soil or other environments where microbes are present.

Generally, the disclosed compositions exhibit antimicrobial activity against gram positive bacteria, gram negative bacteria, viruses, yeast, parasites, rickettsia and molds. Further, the antimicrobial formulation is effective against gram positive bacteria, gram negative bacteria, viruses, yeast, parasites, rickettsia and molds in the presence of biofilms, as well as when the microorganisms are incorporated into or a part of biofilms and an associated biofilm matrix.

The disclosed compositions can also be used for eliminating infections in the thoracic cavity, abdominal cavity, synovial spaces, urinary bladder, lungs, sinus cavities, external auditory canal, oral pharynx, pericardial space, and the like, by microorganisms and viruses. In particular the compositions may be used for elimination of infections including pathogenic microorganisms including Gram negative and positive bacteria, yeast, fungi, rickettsia and the like as well as normally nonpathogenic microorganisms present in the body cavities or spaces, which spaces or cavities do not normally harbor or support the growth of such organisms.

C. Formulations of the Compositions

Also disclosed herein are formulations and kits of the antimicrobial compositions.

The solid antimicrobial composition can be prepared several ways but not limited to physical mixing of the materials and spray drying to form powders, which can be further converted to formulated as pastes, gels, hard compressed tablets, or by addition of water and other additives known in the art, formulated as liquid concentrates. Any of these formulations can be containerized either in small consumer-friendly packaging or larger, bulk institutional sizes (5-20 lb. pails). In addition, premeasured quantities of the dry powders can be packaged in water soluble sachets that dissolve in the presence of water, releasing the materials to form the solution of the antimicrobial composition , such as those provided by Castle Dome Solutions (Castle Dome Solutions, 12426 E. County 8th Street, Yuma, Ariz. 85367) in premeasured quantities for ease of use and dispensing.

The antimicrobial composition may be formulated in aqueous solution along with water soluble and or dispersible inerts such as silica dioxide or titanium dioxide, further surfactants, foaming agents and foam stabilizers, defoaming agents, coloring agents, including dyes and pigment compositions, fragrances (whether natural or synthetically produced), fragrance adjuvants and/or fragrance solubilizers, viscosity modifying agents including thickeners or gelling agents, pH adjusting agents, pH buffers, antioxidants, water softening agents, further solubilizing agents which might be useful in the solubilization of one or more of the constituents in water, preservative compositions, as well as other known art additives not particularly elucidated here.

The compositions can be included in kits that contain premeasured quantities of the antimicrobial solution or the solid composition, along with optional additional materials suitable for the intended end use, such as instructions, appropriate cleaning devices and equipment, deionized water, spray bottles, toweling, applicators, brushes, and the like.

D. Methods of Using the Compositions

The utility of the compositions described herein is as antimicrobials, when prepared in aqueous solution and applied to an unclean, contaminated surface.

The anti-microbial solution can be applied to pre-cleaned surfaces by several methods. Several non-limiting examples include the following:

flood application in which the antimicrobial solution is poured directly on the surface, followed by rinsing and the excess removed after a time sufficient to disinfect the surface, for example from about 30 seconds to about 5 minutes, via a rag or cloth or by suction.

spray application from a low pressure applicator such as a consumer spray bottle such as those offered by M. Jacob & Sons followed by rinsing, with the excess being removed after a time sufficient to disinfect the surface, for example from about 30 seconds to about 5 minutes, by wiping with a cloth or rag or via suction.

high pressure application through a pressure washing system such as those provided by Karcher followed by rinsing and removed after a time sufficient to disinfect the surface, for example from about 30 seconds to about 5 minutes, via rinsing or suction.

clean-in-place (CIP) technology that is used in the food and beverage industry foam application directly to the surfaces followed by rinsing and the excess removed after a time sufficient to disinfect the surface, for example from about 30 seconds to about 5 minutes, by wiping, rinsing, or suction.

Similarly, the anti-microbial solution can be applied to uncleaned surfaces that contain, dirt, grime and biofilms in several methods. Some non-limiting examples include the following:

flood application in which the antimicrobial solution is poured directly on the surface, followed by rinsing and the excess removed after a time sufficient to disinfect the surface, for example from about 30 seconds to about 5 minutes, via a rag or cloth or by suction.

spray application from a low pressure applicator such as a consumer spray bottle such as those offered by M. Jacob & Sons followed by rinsing with the excess being removed after a time sufficient to disinfect the surface, for example from about 30 seconds to about 5 minutes, by wiping with a cloth or rag or via suction.

high pressure application through a pressure washing system such as those provided by Karcher followed by rinsing and removed after a time sufficient to disinfect the surface, for example from about 30 seconds to about 5 minutes, via rinsing or suction.

clean-in-place technology that is used in the food and beverage industry.

foam application directly to the surfaces and removed after the a time sufficient to disinfect the surface, for example from about 30 seconds to about 5 minutes, by wiping, rinsing, or suction.

as a part of the sterilization sequence for medical devices.

added to sonication baths, cleaning trays, and cleaning apparatus for medical devices that are contaminated with human body fluids and materials.

incorporated into dishwashing regimes to provide sanitation for restaurant, institutional, hospitality, and catering operations.

carcass washes where the animal carcass is dipped in the solution for a time sufficient to disinfect the surface, for example from about 30 seconds to about 5 minutes, and then removed and rinsed prior to further processing.

as a general fruit and vegetable wash in which the fruit and vegetables are sprayed or immersed in the solution for the a time sufficient to disinfect the surface, for example from about 30 seconds to about 5 minutes, and the rinsed for further processing.

The anti-microbial solution can also be applied to pre-cleaned surfaces in several methods and not removed after application to provide residual antimicrobial activity by several methods. Some non-limiting examples include the following:

flood application in which the antimicrobial solution is poured directly on the surface and the excess removed after a time sufficient to disinfect the surface, for example from about 30 seconds to about 5 minutes, via a rag or cloth or by suction.

spray application from a low pressure applicator such as a consumer spray bottle such as those offered by M. Jacob & Sons (M. Jacob & Sons, 35601 Veronica, Livonia, Mich. 48150) with the excess being removed after a time sufficient to disinfect the surface, for example from about 30 seconds to about 5 minutes, by wiping with a cloth or rag or via suction.

high pressure application through a pressure washing system such as those provided by Karcher (Kärcher North America, 750 W Hampden Ave. Suite 400, Englewood, Colo. 80110) and removed after a time sufficient to disinfect the surface, for example from about 30 seconds to about 5 minutes, via rinsing or suction.

clean-in-place technology that is used in the food and beverage industry.

foam application directly to the surfaces and the excess removed after a time sufficient to disinfect the surface, for example from about 30 seconds to about 5 minutes, by wiping, or suction.

The antimicrobial solution can be applied to uncleaned surfaces that contain dirt, grime and biofilms in several methods and not removed after application to provide residual antimicrobial activity. Some not limiting examples of these include flood application in which the antimicrobial solution is poured directly on the surface and the excess removed after a time sufficient to disinfect the surface, for example from about 30 seconds to about 5 minutes, via a rag or cloth or by suction.

spray application from a low pressure applicator such as a consumer spray bottle such as those offered by M. Jacob & Sons with the excess being removed after a time sufficient to disinfect the surface, for example from about 30 seconds to about 5 minutes, by wiping with a cloth or rag or via suction.

high pressure application through a pressure washing system such as those provided by Karcher and removed after a time sufficient to disinfect the surface, for example from about 30 seconds to about 5 minutes, via wiping or suction.

clean-in-place technology that is used in the food and beverage industry.

foam application directly to the surfaces and removed after the a time sufficient to disinfect the surface, for example from about 30 seconds to about 5 minutes, by wiping or suction.

part of the sterilization sequence for medical devices.

added to sonication baths, cleaning trays, and cleaning apparatus for medical devices that are contaminated with human body fluids and materials.

incorporated into dishwashing regimes to provide sanitation for restaurant, institutional, hospitality, and catering operations.

animal carcass washes where the animal carcass is dipped in the solution for a time sufficient to disinfect the surface, for example from about 30 seconds to about 5 minutes, and then removed.

general fruit and vegetable wash in which the fruit and vegetables are sprayed or immersed in the solution for a time sufficient to disinfect the surface, for example from about 30 seconds to about 5 minutes, and then further processed.

application by lavage as part of medical procedures to exterior and interior surfaces of the human body that may become exposed to microorganisms, such as skin surfaces, especially in and around wounds, the thoracic cavity, the abdominal cavity, synovial spaces, urinary bladder, lungs, sinus cavities, external auditory canal, oral pharynx, pericardial space, and the like.

In contrast to the common practice used to treat and remove or reduce microbial, yeast, mold, fungus, virus, contamination, namely a 4-step cleaning process, the method disclosed in the current invention comprises only the application of the composition at ambient temperatures and optional rinsing and wiping of the surface with a cloth or other absorbent material. As shown by the results in the experimental section, antimicrobial action occurs within minutes of application.

E. Aspects of the Disclosed Methods

Aspects of the present invention disclose one or more methods for cleaning, a time sufficient to disinfect the surface, for example from about 30 seconds to about 5 minutes, disinfecting and treatment of surfaces with antimicrobial compositions, as well as the compositions themselves. This includes surfaces in which a biofilm is present.

The invention includes as least the following aspects:

Aspect 1: A method of cleaning a surface comprising contacting said surface with a composition comprising
an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and
an organic acid selected from the group consisting of citric acid, tartaric acid, lactic acid and malic acid.

Aspect 2: A method of disinfecting a surface comprising contacting said surface with a composition comprising
an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and
an organic acid selected from the group consisting of citric acid, tartaric acid, lactic acid and malic acid.

Aspect 3: The method of aspects 1-2 where the $C_6$-$C_{10}$ fatty acids salts are a blend of caproic, caprylic and capric acid salts.

Aspect 4: The method of aspect 1-2 where the $C_{12}$-$C_{14}$ fatty acid salts are a blend of lauric and myristic acid salts.

Aspect 5: The method of aspects 1-2 where the $C_6$-$C_{10}$ fatty acids salts are a blend of caproic, caprylic and capric acid salts and where the $C_{12}$-$C_{14}$ fatty acid salts are a blend of lauric and myristic acid salts.

Aspect 6: A method of cleaning a surface comprising contacting said surface with a composition comprising
an organic surfactant derived from the saponification of one or more natural oils and comprising at least about 1-6% caproic, caprylic and capric acid salts, and at least about 30% lauric and myristic acid salts; and
an organic acid selected from the group consisting of citric acid, tartaric acid, lactic acid and malic acid.

Aspect 7: A method of disinfecting a surface comprising contacting said surface with a composition comprising
an organic surfactant derived from the saponification of one or more natural oils and comprising at least about 1-6% caproic, caprylic and capric acid salts, and at least about 30% lauric and myristic acid salts; and
an organic acid selected from the group consisting of citric acid, tartaric acid, lactic acid and malic acid.

Aspect 8: The method of any of aspects 1-7 where a biofilm is present on the surface.

Aspect 9: The method of any of aspects 1-8 for the control of gram positive bacteria, gram negative bacteria, viruses, yeast and molds.

Aspect 10: The method of aspect 9 where the gram positive bacteria, gram negative bacteria, viruses, yeast and molds exist in the presence of biofilms, or are incorporated into biofilms.

Aspect 11: The methods of any of aspects 1-10 further comprising the steps of rinsing of the surface and removal of the excess solution.

Aspect 12: The methods of any of aspects 1-11 where the organic acid is citric acid.

Aspect 13: The methods of any of aspects 1-12 where the natural oils are selected from coconut oil or palm oil.

Aspect 14: The methods of any of aspects 1-13 where the contacting of the surface by the composition is achieved by means of a low pressure applicator or a pressure washer.

Aspect 15: The methods of any of aspects 1-14 where the contacting of the surface by the composition is achieved by means of Clean-In-Place technology.

Aspect 16: The methods of any of aspects 1-15 where the surface is selected from a metallic, textile, plastic, glass, composite, plant material and protein surface.

Aspect 17: The method of aspect 16 where the surface is selected from a surface in the food and beverage industry.

Aspect 18: A method of removing a biofilm from a surface comprising contacting said surface with a composition comprising
an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and
an organic acid selected from the group consisting of citric acid, tartaric acid, lactic acid and malic acid.

Aspect 19: The method of aspect 18 where the $C_6$-$C_{10}$ fatty acids salts are a blend of caproic, caprylic and capric acid salts.

Aspect 20: The method of aspect 18 where the $C_{12}$-$C_{14}$ fatty acid salts are a blend of lauric and myristic acid salts.

Aspect 21: The method of aspect 18 where the $C_6$-$C_{10}$ fatty acids salts are a blend of caproic, caprylic and capric acid salts and where the $C_{12}$-$C_{14}$ fatty acid salts are a blend of lauric and myristic acid salts.

Aspect 22: The method of any of aspects 1-21 wherein the components of the composition are generally regarded as safe (GRAS) by the US FDA for use on food.

Aspect 23: The method of any of aspects 1-21 wherein the components of the composition are acceptable under the regulations of the USDA National Organic Production (NOP).

Aspect 24: An antimicrobial composition consisting essentially of
an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; and
an organic acid selected from the group consisting of citric acid, tartaric acid, lactic acid and malic acid.

Aspect 25: The composition of aspect 24 where the $C_6$-$C_{10}$ fatty acids salts are a blend of caproic, caprylic and capric acid salts.

Aspect 26: The composition of aspect 24 where the $C_{12}$-$C_{14}$ fatty acid salts are a blend of lauric and myristic acid salts.

Aspect 27: The composition of aspect 24 where the $C_6$-$C_{10}$ fatty acids salts are a blend of caproic, caprylic and capric acid salts and where the $C_{12}$-$C_{14}$ fatty acid salts are a blend of lauric and myristic acid salts.

Aspect 28: An antimicrobial composition consisting essentially of
an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts;
an organic acid selected from the group consisting of citric acid, tartaric acid, lactic acid and malic acid; and
water.

Aspect 29: The composition of aspect 28 where the $C_6$-$C_{10}$ fatty acids salts are a blend of caproic, caprylic and capric acid salts.

Aspect 30: The composition of aspect 28 where the $C_{12}$-$C_{14}$ fatty acid salts are a blend of lauric and myristic acid salts.

Aspect 31: The composition of aspect 28 where the $C_6$-$C_{10}$ fatty acids salts are a blend of caproic, caprylic and capric acid salts and where the $C_{12}$-$C_{14}$ fatty acid salts are a blend of lauric and myristic acid salts.

Aspect 32: An antimicrobial composition consisting essentially of
from about 0.5% to about 10% saponified coconut oil as the sodium or potassium salt;
from about 1.0% to about 50% citric acid; and
from about 40% to about 99% water.

Aspect 33: An antimicrobial composition consisting essentially of
about 2% saponified coconut oil as the sodium or potassium salt;
about 10% citric acid; and
about 88% water.

Aspect 34: An antimicrobial solid composition consisting essentially of
from about 0.5% to about 20% of an organic surfactant comprising at least 1-6% caproic, caprylic and capric acid salts, and at least about 30% lauric and myristic acid salts; and
from about 1.0-99.5% citric acid.

Aspect 35: An antimicrobial solid composition consisting essentially of
about 17% saponified coconut oil as the sodium or potassium salt; and
about 83% citric acid.

Aspect 36: The composition of any of aspects 24-36 wherein the components of the composition are generally regarded as safe (GRAS) by the US FDA for use on food.

Aspect 37: The composition of any of aspects 24-37 wherein the components of the composition are acceptable under the regulations of the USDA National Organic Production (NOP).

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Methods for preparing the compounds of this invention are illustrated in the following Examples. Starting materials and the requisite intermediates are in some cases commercially available, or can be prepared according to literature procedures or as illustrated herein.

The Examples are provided herein to illustrate the invention, and should not be construed as limiting the invention in any way.

1. General Methods

General Methods of Preparation of the Compositions

Organic acids (citric, tartaric, lactic and malic acid), the individual surfactants (sodium salts of caproic, caprylic, capric, lauric and myristic acid), or the surfactants derived from saponified natural product oils, (e.g., the sodium salts of saponified coconut or palm oil) were obtained from commercial sources. Aqueous blends of these components were prepared by physical mixing. Aliquots were removed for testing for efficacy against biofilms.

General Methods of Antimicrobial Testing of the Compositions for Efficacy Against Biofilms Testing of the compositions was carried out by MMDG: Life Science Laboratories, 7500 West Henrietta Road, Rush, N.Y. 14543.

Testing was performed in a standard Microbiological laboratory employing standard techniques for handling BSL2 microorganisms. Standard PPE and facility notifications per MMDG procedures were followed.

The following procedures are used to test the antimicrobial efficacy of the compositions as prepared in the Examples below with a contact times of 30 seconds, 1, 5, and 10 minutes and challenged against separate artificially produced biofilm derived from *Escherichia coli* and *Salmonella* spp. and *Staphylococcus aureus*.

Test Surface: Biofilms were developed on borosilicate glass coupons (disks).

Control Articles: Coupons (disks) were exposed to all aspects of preparation including microbial challenge alongside the test surfaces which were exposed to the test article. These surfaces were tested without exposure to the antimicrobial.

Equipment and Materials: The following materials were used as needed :
Trypticase Soy Agar (TSA)
Trypticase Soy Broth (TSB)
Sterile Diluent
Dey-Eng ley Neutralizing Broth (DEB) or equivalent
Spectrophotometer
Colony Counter
Incubators: 30-35° C. and 45-50° C.
Pipette aid
Vortex
CDC Bioreactor
Peristaltic Pump
Sterile tubing
BioSafety Cabinet
*Escherichia coli* ATCC #,and *Salmonella*
General Microbiological glassware and equipment
TS Saline
References: The following serve as references for carrying out the testing using standard procedures:
1. Official Methods of Analysis of AOAC International, 18th edition, 2005
2. Current edition of the United States Pharmacopeia
3. USP <51> Antimicrobial Effectiveness Testing
4. M-060: Challenge Microorganism Preparation, Harvesting and Spectrophotometric Determination
5. S-050.1: General Procedure for Inoculation of Product
6. ASTM E2562-07Standard Test Method for Quantification of *Pseudomonas aeruginosa* Biofilm Grown with High Shear and Continuous Flow using CDC Biofilm Reactor.

EXAMPLE 1

Preparation of Aqueous Composition 1

A blend of saponified coconut oil (2 wt %) and citric acid (10 wt %) was prepared in water (88 wt %) and agitated for 10 min at 20° C. The material was homogeneous.

EXAMPLE 2

Preparation of Additional Aqueous Compositions

Using the identical method described in Example 1 above the compositions appearing in Table 1 are similarly prepared:

TABLE 1

| Composition No. | Acid | Percentage (w/w) | Surfactant | Percentage (w/w) | Water (w/w) |
|---|---|---|---|---|---|
| 2 | Tartaric Acid | 1.0% | Saponified Coconut Oil | 0.5% | 98.5% |
| 3 | Tartaric Acid | 2% | Saponified Coconut Oil | 0.5% | 97.5% |
| 4 | Tartaric Acid | 3% | Saponified Coconut Oil | 0.5% | 96.5% |
| 5 | Tartaric Acid | 5% | Saponified Coconut Oil | 1.0% | 94% |
| 6 | Tartaric Acid | 8% | Saponified Coconut Oil | 1.0% | 91% |
| 7 | Tartaric Acid | 10% | Saponified Coconut Oil | 2% | 88% |
| 8 | Tartaric Acid | 15% | Saponified Coconut Oil | 2% | 83% |
| 9 | Tartaric Acid | 20% | Saponified Coconut Oil | 2% | 78% |
| 10 | Tartaric Acid | 30% | Saponified Coconut Oil | 5% | 65% |
| 11 | Tartaric Acid | 40% | Saponified Coconut Oil | 8% | 52% |
| 12 | Tartaric Acid | 50% | Saponified Coconut Oil | 10% | 40% |
| 13 | Malic Acid | 1.0% | Saponified Coconut Oil | 0.5% | 98.5% |
| 14 | Malic Acid | 2% | Saponified Coconut Oil | 0.5% | 97.5% |
| 15 | Malic Acid | 3% | Saponified Coconut Oil | 0.5% | 96.5% |
| 16 | Malic Acid | 5% | Saponified Coconut Oil | 1.0% | 94% |
| 17 | Malic Acid | 8% | Saponified Coconut Oil | 1.0% | 91% |
| 18 | Malic Acid | 10% | Saponified Coconut Oil | 2% | 88% |
| 19 | Malic Acid | 15% | Saponified Coconut Oil | 2% | 83% |
| 20 | Malic Acid | 20% | Saponified Coconut Oil | 2% | 78% |
| 21 | Malic Acid | 30% | Saponified Coconut Oil | 5% | 65% |
| 22 | Malic Acid | 40% | Saponified Coconut Oil | 8% | 52% |
| 23 | Malic Acid | 50% | Saponified Coconut Oil | 10% | 40% |
| 24 | Citric Acid | 1.0% | Saponified Coconut Oil | 0.5% | 98.5% |
| 25 | Citric Acid | 2% | Saponified Coconut Oil | 0.5% | 97.5% |
| 26 | Citric Acid | 3% | Saponified Coconut Oil | 0.5% | 96.5% |
| 27 | Citric Acid | 5% | Saponified Coconut Oil | 1.0% | 94% |
| 28 | Citric Acid | 8% | Saponified Coconut Oil | 1.0% | 91% |
| 29 | Citric Acid | 10% | Saponified Coconut Oil | 2% | 88% |
| 30 | Citric Acid | 15% | Saponified Coconut Oil | 2% | 83% |
| 31 | Citric Acid | 20% | Saponified Coconut Oil | 2% | 78% |
| 32 | Citric Acid | 30% | Saponified Coconut Oil | 5% | 65% |
| 33 | Citric Acid | 40% | Saponified Coconut Oil | 8% | 52% |
| 34 | Citric Acid | 50% | Saponified Coconut Oil | 10% | 40% |
| 35 | Lactic Acid | 1.0% | Saponified Coconut Oil | 0.5% | 98.5% |
| 36 | Lactic Acid | 2% | Saponified Coconut Oil | 0.5% | 97.5% |
| 37 | Lactic Acid | 3% | Saponified Coconut Oil | 0.5% | 96.5% |
| 38 | Lactic Acid | 5% | Saponified Coconut Oil | 1.0% | 94% |
| 39 | Lactic Acid | 8% | Saponified Coconut Oil | 1.0% | 91% |
| 40 | Lactic Acid | 10% | Saponified Coconut Oil | 2% | 88% |
| 41 | Lactic Acid | 15% | Saponified Coconut Oil | 2% | 83% |
| 42 | Lactic Acid | 20% | Saponified Coconut Oil | 2% | 78% |
| 43 | Lactic Acid | 30% | Saponified Coconut Oil | 5% | 65% |
| 44 | Lactic Acid | 40% | Saponified Coconut Oil | 8% | 52% |

TABLE 1-continued

| Composition No. | Acid | Percentage (w/w) | Surfactant | Percentage (w/w) | Water (w/w) |
|---|---|---|---|---|---|
| 45 | Lactic Acid | 50% | Saponified Coconut Oil | 10% | 40% |
| 46 | Tartaric Acid | 1.0% | Saponified Palm Oil | 0.5% | 98.5% |
| 47 | Tartaric Acid | 2% | Saponified Palm Oil | 0.5% | 97.5% |
| 48 | Tartaric Acid | 3% | Saponified Palm Oil | 0.5% | 96.5% |
| 49 | Tartaric Acid | 5% | Saponified Palm Oil | 1.0% | 94% |
| 50 | Tartaric Acid | 8% | Saponified Palm Oil | 1.0% | 91% |
| 51 | Tartaric Acid | 10% | Saponified Palm Oil | 2% | 88% |
| 52 | Tartaric Acid | 15% | Saponified Palm Oil | 2% | 83% |
| 53 | Tartaric Acid | 20% | Saponified Palm Oil | 2% | 78% |
| 54 | Tartaric Acid | 30% | Saponified Palm Oil | 5% | 65% |
| 55 | Tartaric Acid | 40% | Saponified Palm Oil | 8% | 52% |
| 56 | Tartaric Acid | 50% | Saponified Palm Oil | 10% | 40% |
| 57 | Malic Acid | 1.0% | Saponified Palm Oil | 0.5% | 98.5% |
| 58 | Malic Acid | 2% | Saponified Palm Oil | 0.5% | 97.5% |
| 59 | Malic Acid | 3% | Saponified Palm Oil | 0.5% | 96.5% |
| 60 | Malic Acid | 5% | Saponified Palm Oil | 1.0% | 94% |
| 61 | Malic Acid | 8% | Saponified Palm Oil | 1.0% | 91% |
| 62 | Malic Acid | 10% | Saponified Palm Oil | 2% | 88% |
| 63 | Malic Acid | 15% | Saponified Palm Oil | 2% | 83% |
| 64 | Malic Acid | 20% | Saponified Palm Oil | 2% | 78% |
| 65 | Malic Acid | 30% | Saponified Palm Oil | 5% | 65% |
| 66 | Malic Acid | 40% | Saponified Palm Oil | 8% | 52% |
| 67 | Malic Acid | 50% | Saponified Palm Oil | 10% | 40% |
| 68 | Citric Acid | 1.0% | Saponified Palm Oil | 0.5% | 98.5% |
| 69 | Citric Acid | 2% | Saponified Palm Oil | 0.5% | 97.5% |
| 70 | Citric Acid | 3% | Saponified Palm Oil | 0.5% | 96.5% |
| 71 | Citric Acid | 5% | Saponified Palm Oil | 1.0% | 94% |
| 72 | Citric Acid | 8% | Saponified Palm Oil | 1.0% | 91% |
| 73 | Citric Acid | 10% | Saponified Palm Oil | 2% | 88% |
| 74 | Citric Acid | 15% | Saponified Palm Oil | 2% | 83% |
| 75 | Citric Acid | 20% | Saponified Palm Oil | 2% | 78% |
| 76 | Citric Acid | 30% | Saponified Palm Oil | 5% | 65% |
| 77 | Citric Acid | 40% | Saponified Palm Oil | 8% | 52% |
| 78 | Citric Acid | 50% | Saponified Palm Oil | 10% | 40% |
| 79 | Lactic Acid | 1.0-50% | Saponified Palm Oil | 0.5%-10% | 40%-99% |
| 80 | Lactic Acid | 1.0% | Saponified Palm Oil | 0.5% | 98.5% |
| 81 | Lactic Acid | 2% | Saponified Palm Oil | 0.5% | 97.5% |
| 82 | Lactic Acid | 3% | Saponified Palm Oil | 0.5% | 96.5% |
| 83 | Lactic Acid | 5% | Saponified Palm Oil | 1.0% | 94% |
| 84 | Lactic Acid | 8% | Saponified Palm Oil | 1.0% | 91% |
| 85 | Lactic Acid | 10% | Saponified Palm Oil | 2% | 88% |
| 86 | Lactic Acid | 15% | Saponified Palm Oil | 2% | 83% |
| 87 | Lactic Acid | 20% | Saponified Palm Oil | 2% | 78% |
| 88 | Lactic Acid | 30% | Saponified Palm Oil | 5% | 65% |
| 89 | Lactic Acid | 40% | Saponified Palm Oil | 8% | 52% |
| 90 | Lactic Acid | 50% | Saponified Palm Oil | 10% | 40% |

EXAMPLE 3

Preparation of Solid Compositions

The compositions are be prepared as solids by physically mixing the individual solid components in the proportions shown, or by spray drying an aqueous solution containing the components that have been premixed to provide final the proportions shown. The resulting solid composition is a formulation that is readily dilutable in water and thus reduces the cost of transportation. These solid compositions can also be used to prepare dry powders or sachets that dissolve in the presence of water prior to use, and as a component of antimicrobial kits.

Representative examples appear in Table 2.

TABLE 2

| Composition No. | Acid | Percentage (w/w) | Surfactant | Percentage (w/w) |
|---|---|---|---|---|
| 91 | Tartaric Acid | 1.0 | Saponified Coconut Oil | 0.5% |
| 92 | Tartaric Acid | 10% | Saponified Coconut Oil | 2% |
| 93 | Tartaric Acid | 20% | Saponified Coconut Oil | 3% |
| 94 | Tartaric Acid | 30% | Saponified Coconut Oil | 4% |
| 95 | Tartaric Acid | 40% | Saponified Coconut Oil | 8% |
| 96 | Tartaric Acid | 50% | Saponified Coconut Oil | 10% |
| 97 | Tartaric Acid | 60% | Saponified Coconut Oil | 15% |
| 98 | Tartaric Acid | 70% | Saponified Coconut Oil | 18% |
| 99 | Tartaric Acid | 80% | Saponified Coconut Oil | 20% |
| 100 | Tartaric Acid | 90% | Saponified Coconut Oil | 10% |
| 101 | Lactic Acid | 1.0 | Saponified Coconut Oil | 0.5% |
| 102 | Lactic Acid | 10% | Saponified Coconut Oil | 2% |
| 103 | Lactic Acid | 20% | Saponified Coconut Oil | 3% |
| 104 | Lactic Acid | 30% | Saponified Coconut Oil | 4% |
| 105 | Lactic Acid | 40% | Saponified Coconut Oil | 8% |
| 106 | Lactic Acid | 50% | Saponified Coconut Oil | 10% |

TABLE 2-continued

| Composition No. | Acid | Percentage (w/w) | Surfactant | Percentage (w/w) |
|---|---|---|---|---|
| 107 | Lactic Acid | 60% | Saponified Coconut Oil | 15% |
| 108 | Lactic Acid | 70% | Saponified Coconut Oil | 18% |
| 109 | Lactic Acid | 80% | Saponified Coconut Oil | 20% |
| 110 | Lactic Acid | 90% | Saponified Coconut Oil | 10% |
| 111 | Malic Acid | 1.0 | Saponified Coconut Oil | 0.5% |
| 112 | Malic Acid | 10% | Saponified Coconut Oil | 2% |
| 113 | Malic Acid | 20% | Saponified Coconut Oil | 3% |
| 114 | Malic Acid | 30% | Saponified Coconut Oil | 4% |
| 115 | Malic Acid | 40% | Saponified Coconut Oil | 8% |
| 116 | Malic Acid | 50% | Saponified Coconut Oil | 10% |
| 117 | Malic Acid | 60% | Saponified Coconut Oil | 15% |
| 118 | Malic Acid | 70% | Saponified Coconut Oil | 18% |
| 119 | Malic Acid | 80% | Saponified Coconut Oil | 20% |
| 120 | Malic Acid | 90% | Saponified Coconut Oil | 10% |
| 121 | Citric Acid | 1.0 | Saponified Coconut Oil | 0.5% |
| 122 | Citric Acid | 10% | Saponified Coconut Oil | 2% |
| 123 | Citric Acid | 20% | Saponified Coconut Oil | 3% |
| 124 | Citric Acid | 30% | Saponified Coconut Oil | 4% |
| 125 | Citric Acid | 40% | Saponified Coconut Oil | 8% |
| 126 | Citric Acid | 50% | Saponified Coconut Oil | 10% |
| 127 | Citric Acid | 60% | Saponified Coconut Oil | 15% |
| 128 | Citric Acid | 70% | Saponified Coconut Oil | 18% |
| 129 | Citric Acid | 80% | Saponified Coconut Oil | 20% |
| 130 | Citric Acid | 90% | Saponified Coconut Oil | 10% |
| 131 | Tartaric Acid | 1.0 | Saponified Palm Oil | 0.5% |
| 132 | Tartaric Acid | 10% | Saponified Palm Oil | 2% |
| 133 | Tartaric Acid | 20% | Saponified Palm Oil | 3% |
| 134 | Tartaric Acid | 30% | Saponified Palm Oil | 4% |
| 135 | Tartaric Acid | 40% | Saponified Palm Oil | 8% |
| 136 | Tartaric Acid | 50% | Saponified Palm Oil | 10% |
| 137 | Tartaric Acid | 60% | Saponified Palm Oil | 15% |
| 138 | Tartaric Acid | 70% | Saponified Palm Oil | 18% |
| 139 | Tartaric Acid | 80% | Saponified Palm Oil | 20% |
| 140 | Tartaric Acid | 90% | Saponified Palm Oil | 10% |
| 141 | Lactic Acid | 1.0 | Saponified Palm Oil | 0.5% |
| 142 | Lactic Acid | 10% | Saponified Palm Oil | 2% |
| 143 | Lactic Acid | 20% | Saponified Palm Oil | 3% |
| 144 | Lactic Acid | 30% | Saponified Palm Oil | 4% |
| 145 | Lactic Acid | 40% | Saponified Palm Oil | 8% |
| 146 | Lactic Acid | 50% | Saponified Palm Oil | 10% |
| 146 | Lactic Acid | 60% | Saponified Palm Oil | 15% |
| 148 | Lactic Acid | 70% | Saponified Palm Oil | 18% |
| 149 | Lactic Acid | 80% | Saponified Palm Oil | 20% |
| 150 | Lactic Acid | 90% | Saponified Palm Oil | 10% |
| 151 | Malic Acid | 1.0 | Saponified Palm Oil | 0.5% |
| 152 | Malic Acid | 10% | Saponified Palm Oil | 2% |
| 153 | Malic Acid | 20% | Saponified Palm Oil | 3% |
| 154 | Malic Acid | 30% | Saponified Palm Oil | 4% |
| 155 | Malic Acid | 40% | Saponified Palm Oil | 8% |
| 156 | Malic Acid | 50% | Saponified Palm Oil | 10% |
| 157 | Malic Acid | 60% | Saponified Palm Oil | 15% |
| 158 | Malic Acid | 70% | Saponified Palm Oil | 18% |
| 159 | Malic Acid | 80% | Saponified Palm Oil | 20% |
| 160 | Malic Acid | 90% | Saponified Palm Oil | 10% |
| 161 | Citric Acid | 1.0 | Saponified Palm Oil | 0.5% |
| 162 | Citric Acid | 10% | Saponified Palm Oil | 2% |
| 163 | Citric Acid | 20% | Saponified Palm Oil | 3% |
| 164 | Citric Acid | 30% | Saponified Palm Oil | 4% |
| 165 | Citric Acid | 40% | Saponified Palm Oil | 8% |
| 166 | Citric Acid | 50% | Saponified Palm Oil | 10% |
| 167 | Citric Acid | 60% | Saponified Palm Oil | 15% |
| 168 | Citric Acid | 70% | Saponified Palm Oil | 18% |
| 169 | Citric Acid | 80% | Saponified Palm Oil | 20% |
| 170 | Citric Acid | 90% | Saponified Palm Oil | 10% |

EXAMPLE 4

Evaluation of the Compositions

The evaluation procedure included the following steps:
1. Challenge Organism Preparation A sterile swab of each challenge organism was aseptically taken from stock cultures maintained at 2-8° C. and aseptically transferred to sterile TSA slants. The fresh slants were incubated at 30-35° C. for 18-24 hours.

Ten (10) ml of TS saline was pipetted into each slant subsequent to incubation and the growth mechanically dislodged with a sterile cotton-tipped applicator. The suspension was transferred to a sterile 50 ml polypropylene centrifuge tube. The suspension was washed by centrifugation at 4,000×g for 8-10 minutes. The supernatant was decanted and the pellet suspended in 10 ml of saline TS. The suspension was washed a second time, and suspended in 10 ml of saline TS. The organism concentration was adjusted to ~10⁸ colony forming units (cfu)/ml based on MMDG historical % $T_{620}$ nm spectrophotometer values.

2. Biofilm Generation; CDC Reactor Set and Operation

Coupon preparation: coupons were wiped with sterile 70% IPA to ensure that no residual oils remained on their surface following handling. The reactor was filled to its working volume with 300 mg/L TSB and sterilized in a standard 20-minute liquid steam cycle. The reactor was allowed to cool to room temperature.

Nutritive growth medium (TSB) was prepared at 100 mg/L and sterilized. The reactor was acclimated to room temperature. Using sterile tubing, the reactor was attached to the source of growth medium. A peristaltic pump was placed between the reactor and the media source to modulate the flow rate. Waste was collected in a separate vessel. Sixteen (16) coupons were placed into the reactor representing controls and twelve test surfaces (four each) for each of 3 antimicrobial challenges.

The reactor was seeded with one (1) ml of the challenge organism and, operated statically (batch phase) for 24±8 hours. The peristaltic pump was turned on following the static operation and the reactor was run in continuous flow mode for an additional 24±8 hours at room temperature.

3. Antimicrobial Challenge

Each coupon was removed from the reactor and rinsed gently with sterile TS Saline to remove loosely adhered and planktonic cells. Coupons were placed individually into sterile glass beakers containing 10 ml of the test article. The coupons will be allowed to incubate in the antimicrobial solution at ambient temperature for 30 seconds, one (1), five (5), and ten (10) minutes. Following exposure to the test article, coupons were removed from their respective beakers and placed into 10 ml of sterile DEB in a glass test tube to neutralize the antimicrobial and stop the reaction.

4. Microorganism Recovery

The organisms were removed from the test surfaces and controls through sonication for 20 minutes at room temperature followed by thorough mixing. Serial dilutions of the recovered organisms were performed; 1.0 ml samples of the serial dilutions were plated in duplicate and overpoured with sterile TSA. Plates were incubated under aerobic conditions at 30-35° C. for 3 to 5 days and the recovered organisms quantified.

5. Controls

Recovery Medium Control, Note: applies to liquid suspensions only.

The antimicrobial was diluted 1:10 in DEB. A control sample was prepared using 10 ml of TSB. Both tubes were inoculated with approximately 100 cfu of the challenge organism. One (1) ml samples were plated in duplicate and the recovery in the neutralized medium was compared to that in the TSB Control.

6. Inoculation Control:

The aerobic population of the inoculum will be verified at the time of testing through standard plate count.

7. Calculations

The difference between the log number of microorganisms on the non-treated (no exposure to antimicrobial) materials and that of the corresponding materials exposed to the antimicrobial indicates the reduction in log units.

Log reduction unit=Log A−Log B

Log A=the log number of microorganisms harvested from the non-treated control materials.

Log B=the log number of microorganisms harvested from the corresponding materials exposed to the antimicrobial.

Composition 1 was tested for efficacy with a targeted criteria of a 3 log reduction in the number of microorganisms versus control samples.

As shown in Table 3, the recovery of the microorganism challenge for all three analyses was greater than 50% indicating that the neutralization scheme used in this analysis was effective.

TABLE 3

| | Recovery Medium Control (RMC) | | | | | | | |
|---|---|---|---|---|---|---|---|---|
| Organism | Control | CFU | | Average | Neutralizer | CFU | | Average | % recovery |
| E. coli | TSB | 122 | 147 | 135 | DEB | 109 | 128 | 119 | 88 |
| Salmonella | TSB | 78 | 86 | 82 | DEB | 66 | 70 | 68 | 83 |
| S. aureus | TSB | 39 | 46 | 43 | DEB | 34 | 50 | 42 | 99 |

EXAMPLE 5

Efficacy Against *Escherichia Coli*

Composition 1 was tested against *Escherichia Coli* and showed efficacy after a 5 min period. The results appear in Table 4 and in FIG. 1.

TABLE 4

| | | *Escherichia coli* | | | | | | | |
|---|---|---|---|---|---|---|---|---|---|
| Sample | Dilution | CFU recovered #1 | | CFU recovered #2 | | CFU recovered #3 | | Average | Average × Dilution |
| Control | 1.00E+04 | 51 | 46 | 33 | 69 | 48 | 63 | 52 | 5.17E+05 |
| 30 sec | 1.00E+02 | 79 | 77 | 103 | 94 | 88 | 73 | 86 | 8.57E+03 |
| 1 min | 1.00E+01 | 99 | 81 | 106 | 101 | 97 | 93 | 96 | 9.62E+02 |
| 5 min | 1.00E+00 | 0 | 0 | 0 | 0 | 0 | 0 | 0 | 0.00E+00 |
| 10 min | 1.00E+00 | 0 | 0 | 0 | 0 | 0 | 0 | 0 | 0.00E+00 |

EXAMPLE 6

Efficacy Against *Salmonella* spp

Figure 2:
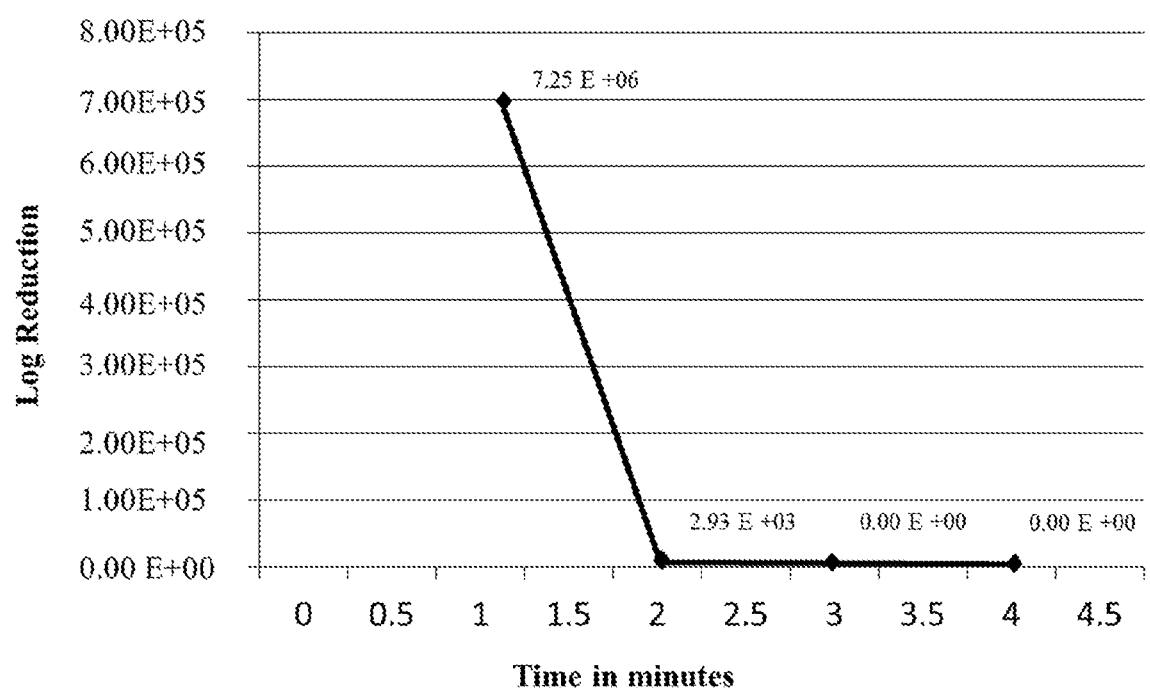
FIG. 2 shows the log reduction vs. time of a *Salmonella* spp. contaminated surface that has been treated with a composition comprising citric acid and saponified coconut oil.

Composition 1 was tested against *Salmonella* spp and showed efficacy after a 5 min period. The results appear in Table 5 and in FIG. 2.

TABLE 5

| | | *Salmonella* spp | | | | | | | |
|---|---|---|---|---|---|---|---|---|---|
| Sample | Dilution | CFU recovered #1 | | CFU recovered #2 | | CFU recovered #3 | | Average | Average × Dilution |
| Control | 1.00E+04 | 51 | 39 | 106 | 101 | 60 | 78 | 73 | 7.25E+05 |
| 1 min | 1.00E+01 | 269 | 301 | 312 | 319 | 285 | 270 | 293 | 2.93E+03 |
| 5 min | 1.00E+00 | 0 | 0 | 0 | 0 | 0 | 0 | 0 | 0.00E+00 |
| 10 min | 1.00E+00 | 0 | 0 | 0 | 0 | 0 | 0 | 0 | 0.00E+00 |

EXAMPLE 7

Efficacy against *Staphylococcus Aureus*

Figure 3:
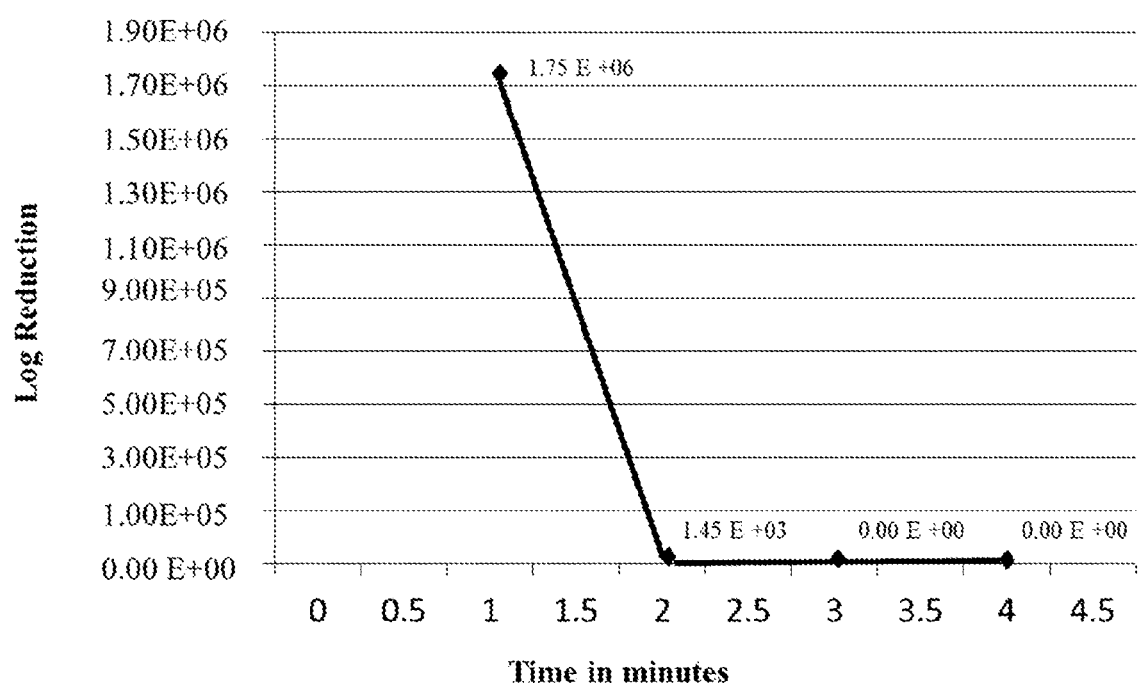
FIG. 3 shows the log reduction vs. time of a *Staphylococcus aureus* contaminated surface that has been treated with a composition comprising citric acid and saponified coconut oil.

Composition 1 was tested against *Staphylococcus aureus* and showed log reductions after a 5 min period. The results appear in Table 6 and in FIG. 3.

TABLE 6

| | | *Staphylococcus aureus:* | | | | | | | |
|---|---|---|---|---|---|---|---|---|---|
| Sample | Dilution | CFU recovered #1 | | CFU recovered #2 | | CFU recovered #3 | | Average | Average × Dilution |
| Control | 1.00E+04 | 194 | 171 | 156 | 183 | 180 | 166 | 175 | 1.75E+06 |
| 1 min | 1.00E+01 | 144 | 157 | 130 | 139 | 155 | 142 | 145 | 1.45E+03 |
| 5 min | 1.00E+00 | 0 | 0 | 0 | 0 | 0 | 0 | 0 | 0.00E+00 |
| 10 min | 1.00E+00 | 0 | 0 | 0 | 0 | 0 | 0 | 0 | 0.00E+00 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition consisting of an organic surfactant comprising a blend of $C_4$-$C_{24}$ saturated and unsaturated fatty acid salts, such that the blend comprises at least about 1-6% $C_6$-$C_{10}$ fatty acids salts, and at least about 30% $C_{12}$-$C_{14}$ fatty acid salts; citric acid; and water wherein the organic surfactant and citric acid are each present in sufficient amounts to achieve at least a 3 log reduction (99.9%) of bacteria on a biofilm-containing environmental surface within two minutes or less.

2. The composition of claim 1 where the $C_6$-$C_{10}$ fatty acids salts are a blend of caproic, caprylic and capric acid salts and where the $C_{12}$-$C_{14}$ fatty acid salts are a blend of lauric and myristic acid salts.

3. A composition consisting of an organic surfactant derived from the saponification of one or more natural oils, said oils consisting of at least 1-6% caproic, caprylic and capric acid salts, and at least 30% lauric and myristic acid salts; citric acid; and water wherein the organic surfactant and citric acid are each present in sufficient amounts to achieve at least a 3 log reduction (99.9%) of bacteria on a biofilm-containing environmental surface within two minutes or less.

4. The composition of claim 3 wherein the surfactant is derived from the saponification of coconut oil.

5. A composition consisting of from about 0.5% to about 10% saponified coconut oil as the sodium or potassium salt; from about 1.0% to about 50% citric acid; and from about 40% to about 99% water;

wherein the saponified coconut oil salt and citric acid are each present in sufficient amounts to achieve at least a 3 log reduction (99.9%) of bacteria on a biofilm-containing environmental surface within two minutes or less.

6. The composition according to claim 5 consisting of from about 1.0% to about 2.0% saponified coconut oil as the sodium or potassium salt; from about 5.0% to about 15.0% citric acid; and from about 83% to about 94% water.

7. The composition according to claim 5 consisting of about 2% saponified coconut oil as the sodium or potassium salt; about 10% citric acid; and about 88% water.

* * * * *